(12) United States Patent
Ohl et al.

(10) Patent No.: US 6,262,344 B1
(45) Date of Patent: Jul. 17, 2001

(54) NEMATODE-INDUCIBLE PLANT GENE PROMOTER

(75) Inventors: Stephan Andreas Ohl, Leiden; Peter Christiaan Sijmons, Amsterdam; Frederique Marianne Van Der Lee, Delft; Oscar Johannes Maria Goddijn, Leiden; Joke Johanna Catharina Klap, Amsterdam, all of (NL)

(73) Assignee: Syngenta Mogen B.V., Leiden (NL)

(*) Notice: Subject to any disclaimer, the term of this patent is extended or adjusted under 35 U.S.C. 154(b) by 0 days.

(21) Appl. No.: 09/117,927

(22) PCT Filed: Jun. 4, 1996

(86) PCT No.: PCT/EP96/02437
§ 371 Date: Apr. 26, 1999
§ 102(e) Date: Apr. 26, 1999

(87) PCT Pub. No.: WO97/46692
PCT Pub. Date: Dec. 11, 1997

(30) Foreign Application Priority Data

Jun. 13, 1995 (EP) .................................................. 95201563

(51) Int. Cl.[7] .......................... C12N 15/84; C12N 15/29; C12N 15/82; C12N 15/31; A01H 5/00
(52) U.S. Cl. .......................... 800/287; 800/278; 800/279; 800/286; 800/288; 800/294; 800/298; 800/317.2; 800/306; 435/6; 435/69.1; 435/419; 435/468; 435/252.3; 435/320.1; 435/199; 536/23.1; 536/23.71; 536/24.1; 536/23.6; 536/23.7; 536/24.5; 47/6
(58) Field of Search .................................... 800/278, 294, 800/298, 306, 279, 286, 287, 288, 317.2; 435/69.1, 468, 419, 252.3, 320.1, 199, 6; 536/23.1, 23.71, 24.1, 23.6, 23.7, 24.5; 47/6

(56) References Cited

FOREIGN PATENT DOCUMENTS

| | | |
|---|---|---|
| 9217054 | 10/1992 | (WO) . |
| 9221757 | 12/1992 | (WO) . |
| 9310251 | 5/1993 | (WO) . |
| 9318170 | 9/1993 | (WO) . |
| 9410320 | 5/1994 | (WO) . |

OTHER PUBLICATIONS

Kim et al. Plant Molecular Biology, vol. 24, pp. 105–117 1994.*

Goddijn, Oscar J.M. et al. "Differential gene expression in nematode–induced feeding structures of transgenic plants harbouring promoter–gusA fusion constructs" *The Plant Journal* 4(5)(1993), pp. 863–873.

Sijmons, Peter C. "Plant–nematode interactions" *Plant Molecular Biology*, vol. 23(1993), pp. 917–931.

Atkinson, Howard J. "Novel Plant Defences Against Nematodes" *Advances in Molecular Plant Nematology*, vol. 268(1994), pp. 197–210.

Niebel, Andreas et al. "Arabidopsis Thaliana as a Model Host Plant to Study Molecular Interactions with Root–Knot and Cyst Nematodes" *Advances in Molecular Plant Nematology*, vol.268(1994), pp. 161–169.

Barthels, N. et al., "Isolation and Analsis of Nematode–Induced Genes in Arabidopsis Thaliana Through In Vivo βGlucuronidase Fusions" *Med. Fac. Landbouww. (Univ. Gnet)*, 59/2b(1994), pp. 757–762.

Karimi, M. et al. "Identification of Root Knot Nematode–Induced Genes in Arabidopsis Thaliana" *Med. Fac. Landbouww. (Univ. Gent)*, pp. 751–756.

* cited by examiner

Primary Examiner—David T. Fox
Assistant Examiner—Medina A. Ibrahim
(74) Attorney, Agent, or Firm—Ladas & Parry

(57) ABSTRACT

An isolated DNA fragment that promotes root knot or cyst nematode indcuible transcription of a coding sequence downstream of and operably linked to the fragment in at least an *Arabidopsis thaliana* plant and a chimeric DNA sequence including the DNA fragment. Also, methods for the use of the DNA fragment.

27 Claims, 8 Drawing Sheets

| Line | Leaf | | | | Primary root | | Secondary root | | | Stem | Flower | | | Seeds |
|---|---|---|---|---|---|---|---|---|---|---|---|---|---|---|
| | Base | Laming | Veins | Rozette | Vasc cyl | Cortex | Base | Vasc cyl | Cortex | Rootip | | Pistil | Pollen Silique | |
| 849-1 | | | | | | | | ▨ | | | | | | |
| 849-2 | | ▨ | ▨ | ▨ | | | | ▨ | | | | | | |
| 849-4 | | ▨ | ▨ | ▨ | | | ▨ | | | | | | | |
| 849-5 | | | | ▨ | ▨ | ▨ | | | ▨ | ▨ | | | | |
| 849-6 | | | | | ▨ | ▨ | ▨ | | | | | | | |
| 849-8 | | ▨ | ▨ | ▨ | | | ▨ | ▨ | | | | | ▨ | ▨ |
| 849-9 | ▨ | ▨ | ▨ | ▨ | | | | | | | | | | |
| 849-10 | | | | | | | | | | | | | | |

Figure 6

```
SEQUENCE LISTING (1) GENERAL INFORMATION:

(iii) NUMBER OF SEQUENCES: 20

(2) INFORMATION FOR SEQ ID NO: 1:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (ii) MOLECULE TYPE: DNA (genomic)

(iii) HYPOTHETICAL: YES
```

```
    (ix) FEATURE:
        (A) NAME/KEY: primer_bind
        (B) LOCATION: 1..20
        (D) OTHER INFORMATION: /note = "primer that anneals to uidA
            gene (Beta-glucuronidase) at position 224-205 from
            the tagging construct pMOG553.(X83420)"

(xi) SEQUENCE DESCRIPTION: SEQ ID NO: 1:

CTTTCCCACC AACGCTGATC                                                   20

(2) INFORMATION FOR SEQ ID NO: 2:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 2:

GTAATGCTCT ACACCACGCC G                                                 21

(2) INFORMATION FOR SEQ ID NO: 3:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: misc_feature
        (B) LOCATION: 1..12
        (D) OTHER INFORMATION: /note = "5'overhang with a XbaI and
            a BamHI site"

(ix) FEATURE:
        (A) NAME/KEY: primer_bind
        (B) LOCATION: 13..35
        (D) OTHER INFORMATION: /note= "this part of the primer
            anneals to sequence 6044-0 at position 646 to 668"

(xi) SEQUENCE DESCRIPTION: SEQ ID NO: 3:

TCTAGAGGAT CCTGGCCATA CAAATCAACG TTTAC                                  35

(2) INFORMATION FOR SEQ ID NO: 4:

(i) SEQUENCE CHARACTERISTICS:
        (A) LENGTH: 2163 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (vi) ORIGINAL SOURCE:
        (A) ORGANISM: Arabidopsis thaliana
        (B) STRAIN: C24

(ix) FEATURE:
        (A) NAME/KEY: CDS
        (B) LOCATION: 2161..2163
        (D) OTHER INFORMATION: /codon_start = 2161
```

(ix) FEATURE:
        (A) NAME/KEY: misc_feature
        (B) LOCATION: 2128..2163
        (D) OTHER INFORMATION: /note = "Sequence of pMOG553
            upstream (5') of the uid A translation initiation
            codon up to the RB/plant genome transition."

(ix) FEATURE:
        (A) NAME/KEY: promoter
        (B) LOCATION: 1..2127

(ix) FEATURE:
        (A) NAME/KEY: primer_bind
        (B) LOCATION: 787..804
        (D) OTHER INFORMATION: /label = primer6044-1
            /note = "annealing of primer 6044-1 (table 4) to
            amplify subfragment"

(ix) FEATURE:
        (A) NAME/KEY: primer_bind
        (B) LOCATION: 1147..1169
        (D) OTHER INFORMATION: /label = primer6044-2
            /note = "annealing of primer 6044-2 (table 4) to
            amplify subfragments"

(ix) FEATURE:
        (A) NAME/KEY: primer_bind
        (B) LOCATION: 1853..1880
        (D) OTHER INFORMATION: /label = primer6044-3
            /note = "annealing of primer 6044-3 (table 4) to
            amplify subfragments"

(ix) FEATURE:
        (A) NAME/KEY: primer_bind
        (B) LOCATION: 1918..1940
        (D) OTHER INFORMATION: /label= primer6044-4
            /note= "annealing of primer 6044-4 (table 4) to
            amplify subfragments"

(ix) FEATURE:
        (A) NAME/KEY: primer_bind
        (B) LOCATION: 1897..1917
        (D) OTHER INFORMATION: /label= primer6044-5
            /note= "annealing of primer 6044-5 (table 4) to
            amplify subfragments (opposite strand)"

(xi) SEQUENCE DESCRIPTION: SEQ ID NO: 4:

```
GAATTCCATC AAATATTAAC TTTTAATATC ACTACATCAT CACCAGATAT GGATGAATAT    60

TTATATAATA TTCACTGCCA ATTAGTTCTT TTAACATATA TATGCTGCTT GTACATATAG   120

GTCATCCAAA TTTTTAGGGT TCAAAACAAA ACCAAAAGAA ACAGAAAAGA TCTGATAAAA   180

AGTCTTCATT TTAGACGAGG GATCAAACTT ATCTAGTGCA TCTGAATGAA AAAAAATGAT   240

CTTAACACTG CAGGTGAAGG CTGGCTCAAT CTTTGACAAT ATATTGATCT GCGATGACCC   300

GGCATATGCA AGAAGCATCG TGGATGACTA TTTTGCCCAA CACAGGGAGG TAGATTTCCA   360

AGTCTTTGTA TATCTTTTTG CTTCTTTTTG GATAAAATCA AGAAGTTTT TTGATCTTGC   420

AAGTGTGTAG TAATTGCAAA TGGATTTTCT GCATGCTATT ATATACGAAA ATGTCTTATT   480

AGTGAATTTG ATATGCTATA TACTTGGCCA TATGCACCAG TCTGAGAAGG AGTTATTTGC   540

GGAAGCAGAG AAAGAAAGAA AAGCTAGAGA AGATGAGGTT TGTAGTTCAC AAAAAAGTTC   600

TTGTTCTCTT TTCAAGTCTT CTCTGTATAT CCTAGTTAAC GAGCATGGCC ATACAAATCA   660

ACGTTTACAG GAAGCTCGGA TAGCACGGGA AGAAGGTGAA CGCAGGCGGA AAGAAAGGGA   720

CCACCGGTAT GGAGACAGGA GGAGGCGTGA CAAACGGGTA AGTACTTATT TGAGTCCAAA   780

TGAATTATAA CCTTCTCAAC TCTGTTTTAT CTGGAAACCA AGTGAGTGAA TATTGTTGGA   840

AATGGTTTGG TTTGTTTTGT TTTGTTTTGC AGCCGAATCC ACGTGATTAT ATGGATGATT   900

ACCATGTAAG TGTTCCTTCT ATCTCAACCA CTTTAAAAAG AATGGTTTAT GCATTTTAGT   960
```

```
ACTGAATCAT CTTAACTGTT CTAAAAATGT AAGTTTGTTA TGATTCTGAA TTTCGTGTAG    1020

GACGAGCTAT GAGGCGCAGA GTGGTGGGCA TTTGGCAAAG CATTGGGGGA AATTATCTAT    1080

ATTTTGCCTT TGAATGTGTA CCTGTTTGTA ATTTCATAAT TTGTAACCTT TTGTATTCAT    1140

ATTCTTATAA TGTATTTTGG CATGAAAACT TGACTTGTTA TTTTTCCCTT CCAATACAAA    1200

AATTCTAAAA TTGGCAAGAA CGACTTACTA CCATGCAGTG ATTTGTGAAG TTTGATAGTG    1260

GTGGTAATTT TAATTGTTTC ACCACAGAAA ATTTCTCTAT ATCCTGAAGA AGATAGCTGA    1320

GTTGAACTGA GAGGTTGGCG TTTCTTAGTG AAAATACAAA AAATAGAAAT CTTTAGCTAG    1380

AAAGTGTGGT GTGGACCCGA CTGATGGTAA CCATGTTCAT TTGGAGGAAC TAATGTGAAT    1440

ATTAGCTAAA AGCATATTGT TGAGTGTTGA CAAAATGACA ACAGATAAAT CGTCAAATAC    1500

TACTCCACCT AGCTAATATT TTTTTTTAAC TAATGTTAGA AAGCCACCTA TTTGCATCCG    1560

TAATGATAAA AACTAAAAAA ATATTAGATT ATTAGAGTGA TACATTTTGT GTGAAAACGT    1620

AAACGAAAGT CAAAGAAAG AAAAACGAAA GAAATTTAAA TGCGGTTTAT GGTGGGCACA    1680

AATGTTGTGA CCTGGTGTGT CCCTTTCCCA CTTAAATGTA CGGCTGATAA TCACATCAGT    1740

GGCGACTTTA GGAAATAGAA AATTCGCACA ATTGACTCGA TACGCATTAA AGTCGTAATC    1800

ACTAGACATT TTTGTTATCT GTCCTTTAGT GGTTCGTTTA ATCTGGAACG TCCTTATAAT    1860

AACATAAGAT AAATATTTAC TTAATTAGCT ACGGAACTAC ATTAGTATTC AATTGATATA    1920

ACTAATGGTA ATTACTAATT AATTGCGGAA AGCCGAGAGG GGTGATGGTG CACGGTGCAT    1980

GTGAAGAGCT TTTGATACGT AAGTGGAGCA CTCATGATAA GCGAAGTTGT CTATTTATAA    2040

AGTTTAATTT ACTGTGCTTT TTATAATGTG ACACACTATT GGAATCCAAT GACTGCATTA    2100

TTTATTTATA TGTAAAAAAA AAAGTCTCAA AGCTTGGATC CCCGGGTAGG TCAGTCCCTT    2160

ATG                                                                 2163
Met
  1
```

(2) INFORMATION FOR SEQ ID NO: 5:

(i) SEQUENCE CHARACTERISTICS:
        (A) LENGTH: 1 amino acids
        (B) TYPE: amino acid
        (D) TOPOLOGY: linear (ii) MOLECULE TYPE: protein (xi) SEQUENCE DESCRIPTION: SEQ ID NO: 5:

```
Met
  1
```

(2) INFORMATION FOR SEQ ID NO: 6:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iii) ANTI-SENSE: NO (ix) FEATURE:
        (A) NAME/KEY: misc_feature
        (B) LOCATION: 1..12
        (D) OTHER INFORMATION: /note = "5' overhang containing the XhoI and the EcoRI sites"

(ix) FEATURE:
        (A) NAME/KEY: primer_bind
        (B) LOCATION: 13..30
        (D) OTHER INFORMATION: /note = "this part of the primer
            anneals the sequence of 6044-0 (SEQIDNO: 4) at
            position 787-804"

(xi) SEQUENCE DESCRIPTION: SEQ ID NO: 6:

CTCGAGAATT CTATAACCTT CTCAACTCTG                                30

(2) INFORMATION FOR SEQ ID NO: 7:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(vi) ORIGINAL SOURCE:
        (A) ORGANISM: Arabidopsis thaliana
        (B) STRAIN: C24

(ix) FEATURE:
        (A) NAME/KEY: misc_feature
        (B) LOCATION: 1..12
        (D) OTHER INFORMATION: /note = "5' overhang containing the
            XhoI and EcoRI site"

(ix) FEATURE:
        (A) NAME/KEY: primer_bind
        (B) LOCATION: 13..35
        (D) OTHER INFORMATION: /note = "this part of the primer
            anneals to the sequence of 6044-0 (SEQIDNO: 4) at
            position 1147-1169"

(xi) SEQUENCE DESCRIPTION: SEQ ID NO: 7:

CTCGAGAATT CTATAATGTA TTTTGGCATG AAAAC                          35

(2) INFORMATION FOR SEQ ID NO: 8:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: misc_feature
        (B) LOCATION: 1..12
        (D) OTHER INFORMATION: /note = "5' overhang containing a
            XhoI and a EcoRI site"

(ix) FEATURE:
        (A) NAME/KEY: primer_bind
        (B) LOCATION: 13..37
        (D) OTHER INFORMATION: /note = "this part of the primer
            anneals to the sequence of 6044-0 (SEQIDNO: 4) at
            position 1853-1880"

(xi) SEQUENCE DESCRIPTION: SEQ ID NO: 8:

CTCGAGAATT CTATAATAAC ATAAGATAAA TATTTAC                        37

(2) INFORMATION FOR SEQ ID NO: 9:

(i) SEQUENCE CHARACTERISTICS:

(A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: misc_feature
        (B) LOCATION: 1..12
        (D) OTHER INFORMATION: /note = "5' overhang containing the
            XhoI and EcoRI site"

(ix) FEATURE:
        (A) NAME/KEY: primer_bind
        (B) LOCATION: 13..35
        (D) OTHER INFORMATION: /note = "part of primer
            annealing to the sequence of 6044-0 (SEQIDNO: 4) at
            position 1918-1940"

(xi) SEQUENCE DESCRIPTION: SEQ ID NO: 9:

CTCGAGAATT CTATAACTAA TGGTAATTAC TAATT                              35

(2) INFORMATION FOR SEQ ID NO: 10:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: misc_feature
        (B) LOCATION: 1..14
        (D) OTHER INFORMATION: /note = "part of primer
            restores sequence of 6044-0 (SEQIDNO: 4) from
            position 2128 to 2142 while causing a deletion of
            fragment 1909 to 2127

(ix) FEATURE:
        (A) NAME/KEY: primer_bind
        (B) LOCATION: 15..35
        (D) OTHER INFORMATION: /note = "this part of the primer
            anneals to the sequence of 6044-0 (SEQIDNO: 4) at
            position 1897-1917"

(xi) SEQUENCE DESCRIPTION: SEQ ID NO: 10:

GGATCCAAGC TTTGATCAAT TGAATACTAA TGTAG                              35

(2) INFORMATION FOR SEQ ID NO: 11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (ix) FEATURE:
        (A) NAME/KEY: primer_bind
        (B) LOCATION: 1..20
        (D) OTHER INFORMATION: /note = "primer that anneals to uidA
            gene (Beta-glucuronidase) at position 224-205 from
            the tagging construct pMOG553.(X83420)"

(xi) SEQUENCE DESCRIPTION: SEQ ID NO: 11:

CTTTCCCACC AACGCTGATC                    20

(2) INFORMATION FOR SEQ ID NO: 12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 12:

CGGACTCTGG ATCCGGAAAG TG                 22

(2) INFORMATION FOR SEQ ID NO: 13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 13:

CTGCTCGAGC CTAGGCACAG GTTATCAACA CGTTTG   36

(2) INFORMATION FOR SEQ ID NO: 14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 14:

CGGACTCTGG ATCCGGAAAG TG                 22

(2) INFORMATION FOR SEQ ID NO: 15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: YES (xi) SEQUENCE DESCRIPTION: SEQ ID NO: 15:

CTTACTCGAG CCATGGTAAG TTTCTGC            27

(2) INFORMATION FOR SEQ ID NO: 16:

(i) SEQUENCE CHARACTERISTICS:
        (A) LENGTH: 44 base pairs
        (B) TYPE: nucleic acid
        (C) STRANDEDNESS: single
        (D) TOPOLOGY: linear

```
        (ii) MOLECULE TYPE: DNA (genomic)

(iii) HYPOTHETICAL: YES (xi) SEQUENCE DESCRIPTION: SEQ ID NO: 16:

GATCTAGACT CGAGAAGCTT GGATCCCCGG GTAGGTCAGT CCCC                    44

(2) INFORMATION FOR SEQ ID NO: 17:

(i) SEQUENCE CHARACTERISTICS:
            (A) LENGTH: 44 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO: 17:

CATGGGGGAC TGACCTACCC GGGGATCCAA GCTTCTCGAG TCTA                    44

(2) INFORMATION FOR SEQ ID NO: 18:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO: 18:

AGCTCGGATC CG                                                       12

(2) INFORMATION FOR SEQ ID NO: 19:

(i) SEQUENCE CHARACTERISTICS:
            (A) LENGTH: 12 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO: 19:

GGCTGCTCGA GC                                                       12

(2) INFORMATION FOR SEQ ID NO: 20:

(i) SEQUENCE CHARACTERISTICS:
            (A) LENGTH: 18 base pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: YES (xi) SEQUENCE DESCRIPTION: SEQ ID NO: 20:

AATTGACGAA GCTTCGTC                                                 18
```

NEMATODE-INDUCIBLE PLANT GENE PROMOTER

This application is a 371 of PCT/EP96/02437 filed on Jun. 4, 1996.

The invention relates to regulatory DNA sequences which can be used for expressing DNA sequences in plant cells. The invention further comprises chimeric DNA comprising said regulatory DNA sequences operably linked to DNA to be expressed in plant cells, as well as plants containing such chimeric DNA in their cells. The invention further relates to methods for making plants that are resistant, or at least less susceptible to plant parasitic nematodes, or their effects, as well as to cells, plants and parts thereof.

STATE OF THE ART

In International patent application WO92/17054, a method is disclosed for the identification and subsequent isolation of nematode responsive regulatory DNA sequences from *Arabidopsis thaliana*.

In WO 92/21757 several regulatory DNA sequences have been isolated from *Lycopersicon esculentum*, which are responsive to the root-knot nematode *Meloidogyne incognita*. Some of these regulatory sequences (LEMMI's, for *Lycopersicon esculentum—Meloidogyne incognita*) are stimulated, whereas others appear to be repressed by the nematode. It is not known whether any of the inducible regulatory sequences are stimulated by a broader range of nematodes.

Another regulatory sequence that is inducible by the root-knot nematode *Meloidogyne incognita* is disclosed in WO 93/06710. A disadvantage of this regulatory sequence TobRb7 is that it is not activated by a number of cyst nematodes, among which the Heterodera and Globodera species. This makes the TobRB7 sequence unsuitable for use in chimeric constructs aiming at, for example, cyst nematode resistance in potato.

It is an object of the invention to provide regulatory DNA sequences which are inducible by both cyst and root knot nematodes and which can be used to express heterologous DNA sequences under their control inside the feeding structure of the nematode, preferably, but not necessarily in a substantially feeding site specific way.

SUMMARY OF THE INVENTION

The invention provides a DNA fragment obtainable from *Arabidopsis thaliana* that is capable of promoting root knot and cyst nematode-inducible transcription of an associated DNA sequence when re-introduced into a plant. Preferred according to the invention are sequences represented by nucleotides 1 to 2141 in SEQ ID NO: 4. Also envisaged are portions or variants of a DNA fragment according to the invention capable of promoting root knot and cyst nematode-inducible transcription of an associated DNA sequence when re-introduced into a plant. A still further preferred aspect of the invention comprises a regulatory DNA fragment that is substantially nematode feeding site-specific.

Further embodiments of the invention comprise chimeric DNA sequences comprising in the direction of transcription a regulatory DNA fragment according to the invention and a DNA sequence to be expressed under the transcriptional control thereof and which is not naturally under transcriptional control of said DNA fragment. Preferred among the chimeric DNA sequences according to the invention are those wherein the DNA sequence to be expressed causes the production of a plant cell-disruptive substance, such as barnase. In a different embodiment the cell-disruptive substance comprises RNA complementary to RNA essential to cell viability. Yet in another embodiment the DNA sequence to be expressed causes the production of a substance toxic to the inducing nematode.

The invention finds further use in a replicon comprising a DNA fragment or chimeric DNA sequence according to the invention, a microorganism containing such a replicon, as well as plant cells having incorporated into their genome a chimeric DNA sequence according to the invention. Further useful embodiments are a root system of a plant essentially consisting of cells according to the invention, as well as full grown plants essentially consisting of cells according to the invention, preferably a dicotyledonous plant, more preferably a potato plant. Also envisaged are plants grafted on a root system according to the invention, as well as plant parts selected from seeds, flowers, tubers, roots, leaves, fruits, pollen and wood and crops comprising such plants.

The invention also encompasses the use of a DNA fragment according to the invention for identifying subfragments capable of promoting transcription of an associated DNA sequence in a plant. Also envisaged is the use of a chimeric DNA sequence according to the invention for transforming plants. The invention further provides the use of a fragment, portion or variant of a regulatory DNA according to the invention for making hybrid regulatory DNA sequences.

The following figures further illustrate the invention.

DESCRIPTION OF THE FIGURES

FIG. 6. Expression patterns outside the NFS of several pMOG849 transformed *Arabidopsis thaliana* lines.

Figure 1:
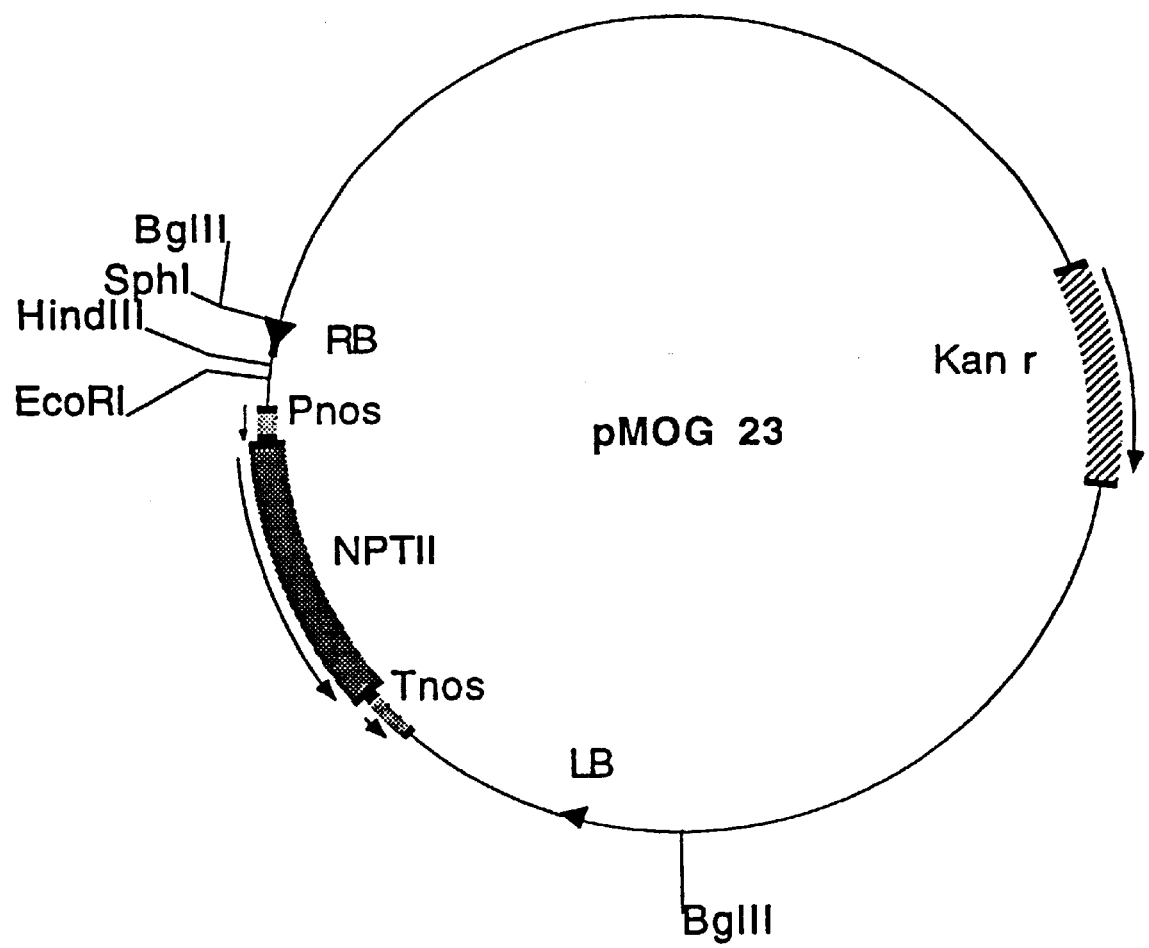
FIG. 1. Schematic plasmid map of Binary vector pMOG23.

Some ways of practicing the invention as well as the meaning of various phrases are explained in more detail below.

DETAILED DESCRIPTION OF THE INVENTION

The present invention provides regulatory DNA sequences obtainable from *Arabidopsis thaliana*, which are inducible by root knot and cyst nematodes and which show a high preference of expression of any associated DNA inside the special nematode feeding structures of the plant root. Such a nematode feeding structure is used by an invading nematode as source of food, whereby the nematode induces a change in the plant tissue thereby forming either a giant cell (root-knot nematodes) or a syncytium (cyst nematodes). A method of isolating regulatory DNA sequences has been disclosed and claimed in a prior application, WO92/17054, which is incorporated herein by reference.

In principle the regulatory DNA sequences according to the invention can be used to express any heterologous DNA in any plant of choice, by placing said DNA under the control of said regulatory DNA sequences and transforming plants with the resulting chimeric DNA sequence using known methods. The heterologous DNA is expressed upon infection of the roots by various root knot nematodes, such as *Meloidogyne incognita*, and cyst nematodes, such as *Heterodera schachtii* and *Globodera pallida* (a more comprehensive, but by no means limiting, list is presented in table 2). Advantageously, the heterologous DNA may consist of a gene coding for a substance that is toxic or inhibitive to a plant parasitic nematode in order to create plants with reduced susceptibility to plant parasitic nematodes. There exist numerous examples of such toxic substances, such as the endotoxins of *Bacillus thuringiensis* (e.g. EP 0 352 052), lectins, and the like.

A more preferred approach for making plants with reduced susceptibility to plant parasitic nematodes consists in the disruption of the specialized feeding structure of the plant roots by expressing a phytotoxic substance under the control of the regulatory DNA sequences according to the invention. The general principles of this approach have been disclosed and claimed in International patent applications WO92/21757, WO93/10251 and WO94/10320, which are hereby incorporated by reference. For the sake of consistency, the phytotoxic substance shall be referred to hereinafter as the nematode feedings site (NFS) disruptive substance.

Although the regulatory DNA sequences according to the invention are substantially specific for the nematode feeding structure, it may be that due to expression in non-target (i.e. non-NFS) tissue the NFS disruptive substances under the control thereof have adverse effects on plant viability and/or yields. Moreover, it was found that the regulatory DNA sequences according to the invention are active during the tissue culture phase in the transformation procedure, necessitating the use of a neutralizing substance during this phase. In order to reduce or eliminate (potential) adverse effects, it is therefore strongly preferred to use a chimeric NFS-disruptive construct according to the invention in conjunction with a neutralizing gene construct. The details of such a so-called two-component approach for the engineering of nematode resistant plants are set out in WO93/10251. According to this approach a NFS-disrupter compound (coding sequence-A) is placed under the control of a promoter that is at least active in the NFS, and preferably not or hardly outside the NFS, whereas the unwanted phytotoxic efects outside the NFS are neutralized by a neutralizing compound (coding sequence-B) that is expressed at least in those tissues wherein the disruptive substance is produced except for the NFS.

According to the two-component approach a suitable promoter-A is defined as a promoter that drives expression of a downstream coding sequence inside the NFS, at levels sufficient to be detrimental to the metabolism and/or functioning and/or viability of the NFS, while this promoter should preferably, but not necessarily, be inactive in tissues outside the NFS; it should at least never be active outside NFS at such levels that the activity of the disruptive substance, encoded by coding sequence-A, can not be neutralized sufficiently by products from coding sequence-B.

The properties of the regulatory DNA sequences according to the invention, in particular the 4, 2.1 and 1.5 kBp fragments of #1164, make them highly useful in the two-component approach, as is illustrated by way of Examples herein. Obviously, numerous mutations such as deletions, additions and changes in nucleotide sequence and/or combinations of those are possible in the regulatory DNA sequences according to the invention which do not alter the properties of these sequences in a way crucial to their intended use. Such mutations do, therefore, not depart from the present invention.

Moreover, as is well known to those of skill in the art, regulatory regions of plant genes consist of disctinct subregions with interesting properties in terms of gene expression. Examples of subregions as meant here, are enhancers but also silencers of transcription. These elements may work in a general (constitutive) way, or in a tissue-specific manner. As is illustrated in the examples, several deletions may be made in the regulatory DNA sequences according to the invention, and the subfragments may be tested for expression patterns of the associated DNA. Various subfragments so obtained, or even combinations thereof, may be useful in methods of engineering nematode resistance, or other applications involving the expression of heterologous DNA in plants. The use of DNA sequences according to the invention to identify functional subregions, and the subsequent use thereof to promote or suppress gene expression in plants is also encompassed by the present invention.

Within the context of this invention, the terms NFS disruptive substance and neutralizing substance embraces a series of selected compounds that are encoded by DNA whose gene products (either protein or RNA or antisense-RNA) are detrimental to the metabolism and/or functioning and/or viability of NFS or organelles therein and for which neutralizing substances are known that are able, when expressed simultaneously in the same cell as the disruptive substance, to repress the activity of the disrupting substance. Preferred combinations of disrupting and neutralizing substances are e.g. barnase/barstar from *Bacillus amyloliquefaciens* (Hartley, 1988, J. Mol. Biol. 202, 913–915), restriction endonucleases/corresponding methylases such as EcoRI from *E.coli* (Green et al., 1981, J. Biol. Chem. 256, 2143–2153) and EcoRI methylase or similar combinations as described in the review for type II restriction modification systems (Wilson, 1991, Nucl. Acid Res. 19, 2539–2566), bacteriocins and corresponding immunity proteins, e.g. colicin E3/immunity protein from *E. coli* (Lau et al. 1985, Nucl. Acid Res. 12, 8733–8745) or any disruptive substance coding gene which may be neutralized by simultaneous production of antisense RNA under control of promoter-B, such as DNA sequences encoding Diptheria Toxin Chain A (Czako & An, 1991, Plant Physiol. 95, 687–692), RNAses such as RNAse T1, ribonucleases or proteases and ribozymes against mRNA that code for phytotoxic proteins.

According to another aspect of the invention combinations of disrupting and neutralizing substances comprise respectively genes inhibitory to an endogenous gene that encodes a protein or polypeptide product that is essential for cell viability and, as a neutralizing gene, a gene that encodes a protein or polypeptide product capable of substituting the function of the endogenous protein or polypeptide product. Such disruptive genes may be selected from the group consisting of (a) genes encoding ribozymes against an endogenous RNA transcript, (b) genes which when transcribed produce RNA transcripts that are complementary or at least partially complementary to RNA transcripts of endogenous genes that are essential for cell viability, a method known as antisense inhibition of gene expression (disclosed in EP-A 240 208), or (c) genes that when transcribed produce RNA transcripts that are identical or at least very similar to transcripts of endogenous genes that are essential for cell viability, an as yet unknown way of inhibition of gene expression referred to as co-suppression (disclosed by Napoli C. et al., 1990, The Plant Cell 2, 279–289).

According to a preferred embodiment of the invention use is made of antisense genes to inhibit expression of endogenous genes essential for cell viability, which genes are expressed in the nematode feeding structures by virtue of regulatory DNA sequences according to the invention fused upstream to the said antisense gene.

The disruptive effect brought about by the antisense gene inhibitory to the vital endogenous gene is neutralized by the expression of a neutralizing compound-B, which expression is under the control of a promoter-B as defined, said compound-B being a protein or polypeptide product which is identical or similar to the protein or polypeptide encoded by the endogenous vital gene and capable of substituting the function of the endogenous gene product in the host plant. It is preferred that the nucleotide sequence of the RNA transcript encoded by the neutralizing gene is divergent from the endogenous vital gene RNA transcript to avoid a possible co-suppressive effect. Hence, it is preferred that the neutralizing gene encodes a protein or polypeptide with essentially the same function as the endogenous vital gene, but through an RNA transcript intermediate that is divergent; neutralizing genes which fit this description can be suitably obtained by screening a database for genes obtainable from a different plant species, or even a different non-plant species, such as yeasts, animal eukaryotes or prokaryotes. Preferably, the nucleotide sequence identity of the transcripts encoded by the disruptive antisense transgene and the neutralizing sense transgene is less than 90%, preferably less than 80%, yet more preferably said neutralizing sense transgene encodes a protein or polypeptide gene product that is not identical in amino acid sequence to the disrupted gene product and wherein the nucleotide sequence identity of the transcripts encoded by the neutralizing transgene is less than 75%.

Target genes for antisense disrupter genes are selected from those coding for enzymes that are essential for cell viability, also called housekeeping enzymes, and should be nuclear encoded, preferably as single copy genes, although a small size gene family would also be suitable for the purpose of the invention. Furthermore, the effect of antisense expression of said genes must not be nullified by diffusion or translocation from other cells or organelles of enzyme products normally synthesized by such enzymes. Preferably, genes coding for membrane-translocating enzymes are chosen as these are involved in establishing chemical gradients across organellar membranes. Inhibition of such proteins by antisense expression can not, by definition, be cancelled by diffusion of substrates across the membrane in which these proteins reside. The translocated compound is not limited to organic molecules but can be of inorganic nature; e.g. P, H, OH or electrons.

Preferably, the membrane-translocating enzymes should be present in organelles that increase in numbers during parasitism, thereby illustrating the essential role that such organelles have in cells comprising the NFS. Specific examples for such organelles are mitochondria, endoplasmic reticulum and plasmodesmata (Hussey et al. 1992 Protoplasma 167; 55–65, Magnusson & Golinowski 1991 Can. J. Botany 69; 44–52). A list of target enzymes is given in Table 1 by way of example but the invention is not limited to the enzymes mentioned in this table. More detailed listings can be assembled from series as Biochemistry of Plants (Eds. Stumpf & Conn, 1988–1991, Vols. 1–16 Academic Press) or Encyclopedia of Plant Physiology (New Series, 1976, Springer-Verlag, Berlin).

Although only in some cases, the genes coding for these enzymes have been isolated and, therefore, the number of gene copies are not known, the criteria that have to be met are described in this invention.

TABLE 1

EXAMPLES OF TARGET ENZYMES FOR ANTISENSE EXPRESSION IN NFS AND SENSE EXPRESSION OUTSIDE NFS

| enzyme | pathway/organelle |
| --- | --- |
| ATP synthase | mitochondrion |
| adenine nucleotide translocator | mitochondrion |
| phosphate translocator | mitochondrion |
| tricarboxylate translocator | mitochondrion |
| dicarboxylate translocator | mitochondrion |
| 2-oxo-glutarate translocator | mitochondrion |
| cytochrome C | mitochondrion |
| pyruvate kinase | glycolysis |
| glyceraldehyde-3P-dehydrogenase | glycolysis |
| NADPH-cytochrome P450 reductase | lipid metabolism |
| fatty acid synthase complex | lipid metabolism |
| glycerol-3P-acyltransferase | lipid metabolism |
| hydroxymethyl-glutaryl CoA reductase | mevalonic acid pathway |
| aminoacyl transferase | nucleic acid metabolism |
| transcription factors | nucleic acid metabolism |
| elongation factors | nucleic acid metabolism |

A suitable promoter-B is defined as a promoter that drives expression in substantially all cells wherein coding sequence-A is expressed, with the proviso that it does not drive expression inside a nematode feeding structure, or not effectively. (With 'substantially all cells' is meant at least those cells that should be viable in order to get normal plant growth and or development required for commercial exploitation of such plants). As an illustration of plants in which the disruptive effect is not neutralized in exactly all cells of the host plant and which are nevertheless viable and suitable for commercial exploitation, are those which express a disrupter gene according to this invention in stamen cells; this may yield male-sterile plants, which is even regarded as a commercially attractive trait in some crops. Suitable examples of the promoter-B type can be obtained from plants or plant viruses, or may be chemically synthesized. The regulatory sequences may also include enhancer sequences, such as found in the 35S promoter of CaMV (Kay et al., 1987, Science 236, 1299–1302), and mRNA stabilizing sequences such as the leader sequence of Alfalfa Mosaic Virus RNA4 (Brederode et al., 1980, Nucl. Acids Res. 8, 2213–2223) or any other sequences functioning in a like manner.

Alternatively, to provide for expression in all or effectively all plant tissues, a promoter-B/coding-sequence-B can be complemented with a second promoter-B'/coding-sequence-B having an expression pattern which is partly overlapping or entirely complementary to promoter-B/coding-sequence-B, with the proviso that neither promoter-B nor promoter-B' drives expression in the NFS. Also hybrid promoters, comprising (parts of) different promoters combined as to provide for the required expression pattern as defined herein, fall within the scope of the present invention.

Preferebly, promoter-B is the Cauliflower Mosaic Virus 35S promoter or derivatives thereof, which is generally considered to be a strong constitutive promoter in plant tissues (Odell et al. 1985 Nature 313, 810–812). Another preferred example for promoter-B is the strong root promoter rolD (Leach & Aoyagi 1991 Plant Sci. 79; 69–76) from plasmid pRiA4 of *Agrobacterium rhizogenes*; the 5' flanking region of ORF15 (Slightom et al. 1986, J. Biol. Chem. 261, 108–121). The suitability of other constitutive promoters such as the nopaline synthase promoter (Bevan, 1984, Nucl. Acids Res. 12, 8711–8721) or figwort mosaic virus promoter (EP-A 426 641) for use as promoter-B can be tested through fusion to marker genes such as GUS (Jefferson, 1987, Plant Mol. Biol. Reporter 5, 387–405), transfer of these constructs to plants and histochemical analysis of such transgenic plants after infection with PPN.

Other regulatory sequences such as terminator sequences and polyadenylation signals include any such sequence functioning as such in plants, the choice of which is within the level of skill of the average skilled person in the art. An example of such sequences is the 3' flanking region of the nopaline synthase (nos) gene of *Agrobacterium tumefaciens* (Bevan, 1984, Nucl. Acids Res. 12, 8711–8721).

Further details of the two component approach can be found in WO93/10251 (herein incorporated by reference).

The choice of the plant species is primarily determined by the amount of damage through PPN infections estimated to occur in agriculture and the amenability of the plant species to transformation. Plant genera which are damaged during agricultural practice by PPN and which can be made significantly less susceptible to PPN by ways of the present invention include but are not limited to the genera mentioned in Table 2.

Nematode species as defined in the context of the present invention include all plant-parasitic nematodes that modify host cells into specially adapted feeding structures which range from migratory ectoparasites (e.g. Xiphinema spp.) to the more evolved sedentary endoparasites (e.g. Heteroderidae, Meloidogynae or Rotylenchulinae). A list of parasitic nematodes are given in Table 2, but the invention is not limited to the species mentioned in this table. More detailed listings are presented in Zuckerman et al. (eds., in: Plant Parasitic Nematodes, Vol. I 1971, New York, pp. 139–162).

TABLE 2

EXAMPLES OF PLANT-PARASITIC NEMATODES AND THEIR PRINCIPAL HOST PLANTS

| Nematode Species | Principal Host Plants |
|---|---|
| Meloidogyne | |
| M. hapla | wide range |
| M. incognita | wide range |
| M. exigua | coffee, tea, Capsicum, Citrullus |
| M. indica | Citrus |
| M. javanica | wide range |
| M. africana | coffee |
| M. graminis | cereals, grasses |
| M. graminicola | rice |
| M. arenaria | wide range |
| Heterodera & Globodera | |
| H. mexicana | Lycopersicon esculentum, Solanum spp. |
| H. punctata | cereals, grasses |
| G. rostochiensis | Solanum tuberosum, Solanum spp, Lycopersicon esculentum |
| G. pallida | Solanum tuberosum |
| G. tabacum | Nicotiana tabacum, Nicotiana spp. |
| H. cajani | Cajanus cajan, Vigna sinensis |
| H. glycines | Glycine max, Glycine spp. |
| H. oryzae | Oryza sativa |
| H. schachtii | Beta spp, Brassica spp, |
| H. trifolii | Trifolium spp. |

TABLE 2-continued

EXAMPLES OF PLANT-PARASITIC NEMATODES AND THEIR PRINCIPAL HOST PLANTS

| Nematode Species | Principal Host Plants |
|---|---|
| H. avenae | cereals, grasses |
| H. carotae | Daucus carota |
| H. cruciferae | Cruciferae |
| H. goettingiana | Pisum sativum, Vicia spp. |

Within the context of this invention, a plant is said to show reduced susceptibility to plant parasitic nematodes (PPN) if a statistically significant decrease in the number of mature females developing at the surface of plant roots can be observed as compared to control plants. Susceptible/resistance classification according to the number of maturing females is standard practice both for cyst- and root-knot nematodes (e.g. LaMondia, 1991, Plant Disease 75, 453–454; Omwega et al., 1990, Phytopathol. 80, 745–748).

A nematode feeding structure according to the present invention shall include an initial feeding cell, which shall mean the cell or a very limited number of cells destined to become a nematode feeding structure, upon induction of the invading nematode.

A NFS disruptive effect according to the invention is not limited to adverse effects on the NFS only; also disruptive effects are contemplated that, in addition, have an adverse effect on nematode development by way of direct interaction.

Several techniques are available for the introduction of recombinant DNA containing the DNA sequences as described in the present invention into plant hosts. Such techniques include but are not limited to transformation of protoplasts using the calcium/polyethylene glycol method, electroporation and microinjection or (coated) particle bombardment (Potrykus, 1990, Bio/Technol. 8, 535–542).

In addition to these so-called direct DNA transformation methods, transformation systems involving vectors are widely available, such as viral vectors (e.g. from the Cauliflower Mosaic Virus (CaMV) and bacterial vectors (e.g. from the genus Agrobacterium) (Potrykus, 1990, Bio/Technol. 8, 535–542). After selection and/or screening, the protoplasts, cells or plant parts that have been transformed can be regenerated into whole plants, using methods known in the art (Horsch et al., 1985, Science 225, 1229–1231). The choice of the transformation and/or regeneration techniques is not critical for this invention.

According to a preferred embodiment of the present invention use is made of so-called binary vector system (disclosed in EP-A 120 516) in which Agrobacterium strains are used which contain a helper plasmid with the virulence genes and a compatible plasmid, the binary vector, containing the gene construct to be transferred. This vector can replicate in both *E.coli* and in Agrobacterium; the one used here is derived from the binary vector Bin19 (Bevan, 1984, Nucl. Acids Res. 12, 8711–8721). The binary vectors as used in this example contain between the left- and right-border sequences of the T-DNA, an identical NPTII-gene coding for kanamycin resistance (Bevan, 1984, Nucl. Acids Res. 12, 8711–6721) and a multiple cloning site to clone in the required gene constructs.

Recent scientific progress shows that in principle monocots are amenable to transformation and that fertile transgenic plants can be regenerated from transformed cells. The development of reproducible tissue culture systems for these crops, together with the powerful methods for introduction of genetic material into plant cells has facilitated transformation. Presently, preferred methods for transformation of monocots are microprojectile bombardment of explants or suspension cells, and direct DNA uptake or electroporation (Shimamoto, et al., 1989, Nature 338, 274–276). Transgenic maize plants have been obtained by introducing the *Streptomyces hygroscopicus* bar gene, which encodes phosphinothricin acetyltransferase (an enzyme which inactivates the herbicide phosphinothricin), into embryogenic cells of a maize suspension culture by microparticle bombardment (Gordon-Kamm, 1990, Plant Cell, 2, 603–618). The introduction of genetic material into aleurone protoplasts of other monocot crops such as wheat and barley has been reported (Lee, 1989, Plant Mol. Biol. 13, 21–30). Wheat plants have been regenerated from embryogenic suspension culture by selection only the aged compact and nodular embryogenic callus tissues for the establishment of the embryogenic suspension cultures (Vasil, 1990 Bio/Technol. 8, 429–434). Also an Agrobacterium-using method for the transformation of rice has been disclosed recently (WO 95/16031). The combination with transformation systems for these crops enables the application of the present invention to monocots. These methods may also be applied for the transformation and regeneration of dicots.

The following examples are given only for purposes of illustration and do not intend to limit the scope of the invention.

EXPERIMENTAL PART

DNA Procedures

All DNA procedures were carried out according to standard methods described in Maniatis (Molecular Cloning, A laboratory Manual 2nd Edition, Cold Spring Harbor Laboratory, 1990).

Transformation of Arabidopsis

Transformation was carried out using co-cultivation of *Arabidopsis thaliana* (ecotype C24) root segments with Agrobacterium strain MOG101 containing a suitable binary vector as described by Valvekens et al. (1988, Proc. Nat. Acad. Sci. USA 85, 5536–5540) which is as follows:

Arabidopsis seeds were vernalized for 7 days at 4° C. before germination. Seeds were surface-sterilized for 2 min in 70% EtOH, transferred to 5% NaOCl/0.5% NaDodSO$_4$ for 15 min rinsed five times with sterile distilled water, and placed on 150×25 mm Petri dishes containing germination medium (GM) (Table 3) to germinate. Petri dishes were sealed with gas-permeable medical tape (Urgopore, Chenove France). Plants were grown at 22° C. in a 16-hr light/8-hr dark cycle. The same growth-room conditions were used for tissue culture procedures. All plant media were buffered with 2-(N-morpholino)ethanesulfonic acid at 0.5 g/liter (pH 5.7: adjusted with 1 M KOH), solidified with 0.8% Difco Bacto agar, and autoclaved at 121° C. for 15 min. Hormones and antibiotics were dissolved in dimethyl sulfoxide and water, respectively, and were added to the medium after autoclaving and cooling to 65° C.

Intact roots were incubated for 3 days on solidified 0.5/0.05 medium (Table 3). Roots were then cut into small pieces of about 0.5 cm (herein referred to as "root explants") and transferred to 10 ml of liquid 0.5/0.05 medium; 0.5–1.0 ml of an overnight Agrobacterium culture was added. The root explants and bacteria were mixed by gentle shaking for about 2 min.

Subsequently, the root explants were blotted on sterile filter paper to remove most of the liquid medium and cocultivated for 48 hr on 0.5/0.05 agar. The explants were then rinsed in liquid 0.5/0.05 medium containing 1000 mg of vancomycin (Sigma) per liter. The pieces were blotted and then incubated on 0.15/5 agar (Table 3) supplemented with 750 mg of vancomycin and 50 mg of Km per liter. Three weeks after infection with agrobacteria containing a chimeric neo gene, green Km-resistant (Km$^R$) calli were formed in a background of yellowish root explants. At this point the root explants were transferred to fresh 0.15/5 agar containing only 500 mg of vancomycin and 50 mg of Km per liter. Three weeks later most green call had formed shoots. Transformed shoots were transferred to 150×25 mm Petri dishes containing GM to form roots or seeds or both. In these Petri dishes, many regenerants formed seeds without rooting. Rooted plants could also be transferred to soil to set seed. The following modification was made to obtain the initial root material 6 sterilized *Arabidopsis thaliana* C24 seeds were germinated in 50 ml GM (250 ml Erlenmeyer) on a rotary shaker (100 rpm) in a growth room for 9 days under low light conditions. Transgenic plants were regenerated from shoots grown on selection medium (50 mg/l kanamycin), rooted and transferred to germination medium or soil.

TABLE 3

PLANT MEDIA

|  | CIM | | | | SIM | |
| --- | --- | --- | --- | --- | --- | --- |
|  | GM | R3* | PG1* | 0.5/0.05 | 0.05/7* | 0.15/5* |
| Salts + vitamins | MS | MS | B5 | B5 | MS | B5 |
| Sucrose, g/L | 10 | 30 | — | — | 30 | — |
| Glucose, g/L | — | — | 20 | 20 | — | 20 |
| IAA, mg/L | — | 5 | — | — | 0.05 | 0.15 |
| 2,4-D, mg/L | — | 0.5 | 2 | 0.5 | — | — |
| 2ipAde, mg/L | — | — | — | — | 7 | 5 |
| Kin, mg/L | — | 0.3 | 0.05 | 0.05 | — | — |

L,liter; IAA, indole-3-acetic acid; Kin, kinetin; 2ipAde, N$^6$-(2-isopentenyl) adenine; CIM, callus-inducing medium; SIM, shoot-inducing medium; MS, Murashige & Skoog medium; B5, Gamborg B5 medium Transformation of Potato For the transformation of *Solanum tuberosum* var. Kardal a protocol as described in Hoekema et al. 1989 Bio/Technology 7, 273–278 was used with several modifications.

Peeled surface-sterilized potato tubers were cut in 2 mm thick slices. These were used to cut out disks of 1 cm in diameter around the periphery of the slice. The disks were collected in WM (Murashige & Skoog medium, containing 1 mg/l thiamine HCl, 0.5 mg/l pyridoxine Hcl, 0.5 mg/l nicotinic acid, 100 mg/l myo-inositol, 30 g/l sucrose, 0.5 g/l MES pH 5.8). Inoculation with *Agrobacterium tumefaciens* strain EHA105 (Hood et al. 1993 Transgenic Research 2, 208–218) was done by replacing the WM with 100 ml fresh WM containing the resuspended pellet of 10 ml Agrobacterium culture grown freshly in LB+appropriate antibiotic to an OD$_{600}$ of 0.5–0.7. After incubating the tuber disks for 20 min in the bacterium suspension they were transferred to solidified CM (WM supplemented with 8 g/l agar, 3.5 mg/l zeatin riboside, 0.03 mg/l indole acetic acid) at a density of 20 explants/petridish. After two days the disks were transferred to PM (CM supplemented with 200 mg/l cefotaxime, 100 mg/l vancomycin) to select against the Agrobacteria. Three days later the disks were transferred to SIM plates (CM supplemented with 250 mg/l carbenicillin, 100 mg/l kanamycin) at a density of 10 explants/petridish to select for the regeneration of transformed shoots. After 2 weeks the tissue disks were transferred to fresh SIM, and after another 3 weeks they were transferred to SEM (SIM with 10×lower concentration of hormones). About 8–9 weeks after co-cultivation the shoots were large enough to cut them from the callus tissue and transfer them to glass tubes (Sigma, Cat.nr. C5916) containing 10 ml of RM (WM containing 0.5×MS salts, 0.5×vitamins, 10 g/l sucrose, 100 mg/l cefotaxime, 50 mg/l vancomycin and 50 mg/l kanamycin) for rooting maintenance in vitro and vegetative propagation.

Handling of Nematodes, Growth and Infection of Plant Roots

Arabidopsis seeds were surface sterilized and sown in petri dishes (Ø: 9 cm) on B5 medium containing 20 g/l glucose and 20 mg/l kanamycin. After 3 days at 4° C. the plates were incubated for 2 weeks in a growth chamber at 22° C. with 16-hr light/8 hr-dark cycle. Kanamycin-resistant plants were then transferred to soil-filled translucent plastic tubes (30×15×120 mm, Kelder plastibox b.v., The Netherlands). The tubes were placed tilted at an angle of 60 degrees to the vertical axis causing the roots to grow on the lower side of the tubes. This allows to monitor the infection process by eye and facilitates removal of the root system from the soil for GUS analysis. Infection was done after two more weeks by injecting a suspension containing 500 second stage larvae of *Heterodera schachtii* (in 3 ml $H_2O$) per root system or 300 second stage larvae of *Meloidogyne incognita* per root system into the soil. Similarly, potato shoots which had rooted on kanamycin-containing RM medium were transferred to soil-filled translucent plastic tubes (30×15× 120 mm, Kelder plastibox b.v., The Netherlands) and grown tilted for another 2 weeks at 22° C. with 16 h light/8 h dark cycle. Infection was done by injecting a suspension containing 500 second stage larvae of *Globodera pallida* (in 3 ml $H_2O$) per root system into the soil.

GUS Assay

GUS activity was determined at various times during the infection process by thoroughly washing the root systems to remove most of the adhering soil and incubating them in X-Gluc solution (1 mg/ml X-Gluc, 50 mM $NaPO_4$ (pH7), 1 mM $K_4Fe(CN)_6$, 1 mM K $K_3Fe(CN)_6$, 10 mM EDTA, 0.1% Triton X100) at 37° C. over night. After removal of the chlorophyll from the tissue by incubation with 70% ethanol for several hours GUS staining was monitored under the microscope.

EXAMPLE 1

Construction of Binary Vector pMOG800

Figure 2:
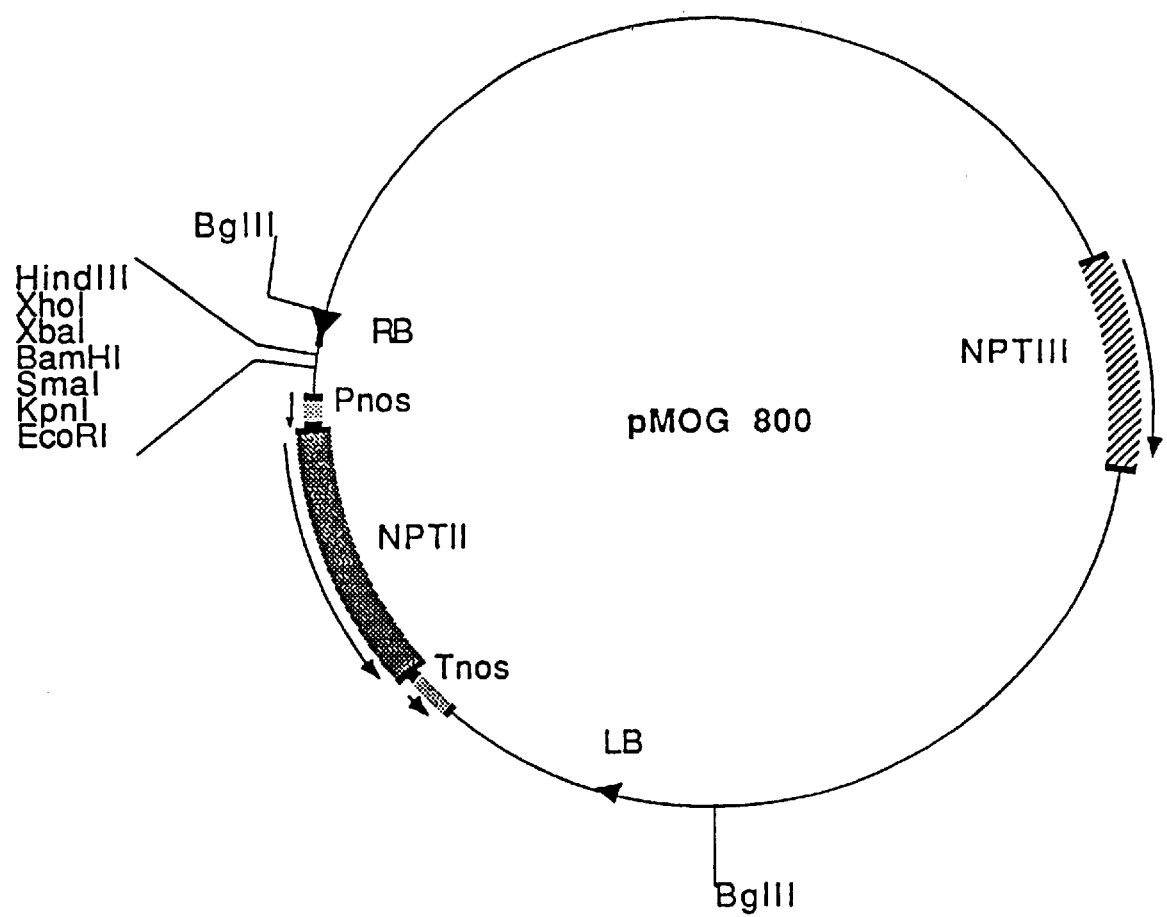
FIG. 2. Schematic plasmid map of Binary vector pMOG800.

The binary vector pMOG800 is a derivative of pMOG23 (FIG. 1, deposited at the Centraal Bureau voor schimmelcultures, Oosterstraat 1, Baarn, The Netherlands on Jan. 29, 1990 under number CBS 102.90) in which an additional KpnI restriction site was introduced into the polylinker between EcoRI and SmaI. This plasmid contains between the left and right borders of T-DNA a kanamycin resistance gene for selection of transgenic plant cells (FIG. 2). A sample of *E. Coli* DH5 alpha, harbouring pMOG800, was deposited at the Centraal Bureau voor Schimmelcultures, Oosterstraat 1, Baarn, The Netherlands, on Aug. 12, 1993 under number CBS 414.93.

EXAMPLE 2

Construction of Promoterless GUS Construct pMOG553

Figure 3:
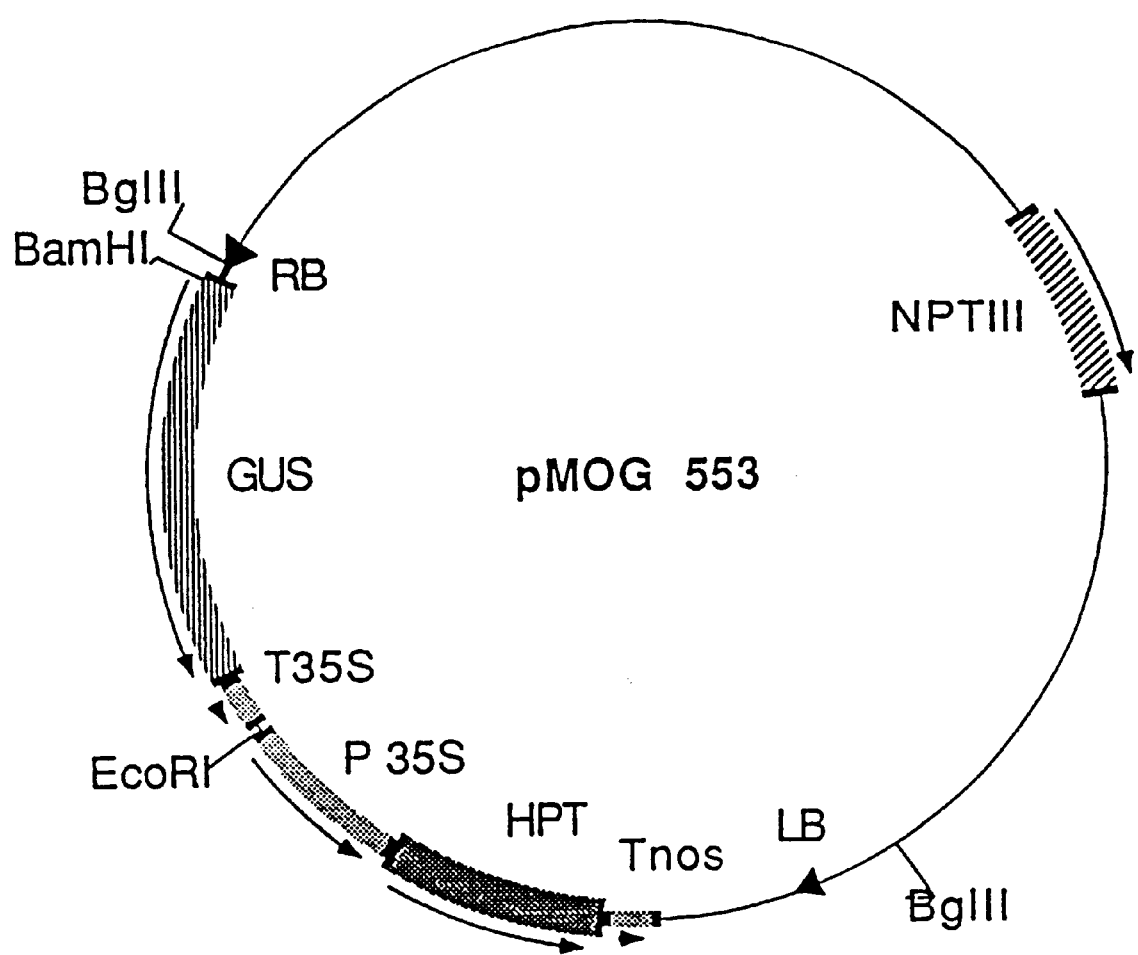
FIG. 3. Schematic plasmid map of Binary vector pMOGS53.

Construction of this vector is described in Goddijn et al. 1993 Plant J 4, 863–873. In this reference an error occurs; the construct contains a CaMV 35S RNA terminator behind the β-glucuronidase gene instead of the indicated nos terminator. The sequence between the T-DNA borders of this binary vector is available from the EMBL database under accession number: X84105.pMOG553 carries the HygR marker for plant transformation (FIG. 3).

EXAMPLE 3

Identification and Isolation of a Trapped NFS-preferential Promoter Fragment in *Arabidopsis thaliana*

The binary vector pMOG553 was mobilized by triparental mating to *Agrobacterium tumefaciens* strain MOG101. The resulting strain was used for Arabidopsis root transformation. More than 1100 transgenic Arabidopsis plant lines were obtained in this way. Transgenic plants were grown to maturity, allowed to self-fertilize and the resulting seeds (51) were harvested and vernalized. Subsequently S1 seeds were germinated on nutrient solution (Goddijn et al. 1993 Plant J 4, 863–873) solidified with 0.6% agar, 10 mg/l hygromycin and stored at 4° C. for a 4 day imbibition period. At day 5 the plates were transferred to room temperature and moderate light (1000 lux, 16 h L/8 h D) for germination. Fourteen days old seedlings were transferred to potting soil in tilted translucent plastic tubes (30×15×120 mm) for further growth at 5000 lux (20° C.). Growing the plants in this way causes most of the root system to grow on the lower side of the tubes in the interphase between soil and tube. After two weeks the roots were infected with nematodes as described in the Experimental part. At several time points after inoculation (ranging from 2–14 days), the root systems were analyzed for GUS activity as described in the Experimental part. Line pMOG553#1164 was identified as a line which showed rather strong GUS expression inside syncytia and giant cells induced by *Heterodera schachtii* and *Meloidogyne incognita*, respectively. In un-infected control plants (as well as in the infected plants) of this line very weak GUS expression was detected in a few cells at the base of young lateral roots and in some green parts of the plant.

In line 1164 this phenotype was found to segregate at a 1:3 ratio, indicating that the GUS construct is present at one locus per genome. The presence of only one T-DNA copy was confirmed by Southern analysis. A 1.5 kb fragment of the trapped promoter sequence adjacent to the GUS open reading frame was isolated by inverted PCR. Genomic DNA of this line was cleaved with the restriction enzyme MscI, which cleaves once in the GUS coding region, and religated. By subsequent digestion of the circular DNA with the enzyme SnaBI a linear fragment was obtained with known GUS sequences at the ends and the flanking plant sequence in between. This fragment was amplified using the primer set GUSinv5 (5' CTT TCC CAC CAA CGC TGA TC 3' SEQ ID NO: 1) and GUS7 (5' GTA ATG CTC TAC ACC ACG CCG 3' SEQ ID NO: 2), cloned in a multi-copy vector and sequenced (see below). To clone this amplified fragment back in front of GUS the plant sequence was re-amplified from Arabidopsis genomic DNA using the primers GUSinv5 and 1164XBM (5' TCT AGA GGA TCC TGG CCA TAC AAA TCA ACG TTT AC 3' SEQ ID NO: 3). A pfu DNA polymerase carrying a proofreading activity was used to reduce the error rate. Primer 1164XBM introduces a BamHI site at the 5 end of the promoter, which allowed to clone the 1480 bp BamHI promoter fragment back in front of GUS in construct pMOG819 without changing the sequence between the GUS open reading frame and the plant promoter.

EXAMPLE 4

Construction of Promoterless GUS Construct pMOG819

This vector was constructed by cloning the GUSintron coding region (Vancanneyt et al. 1990, Mol. Gen. Genet.

Figure 4:
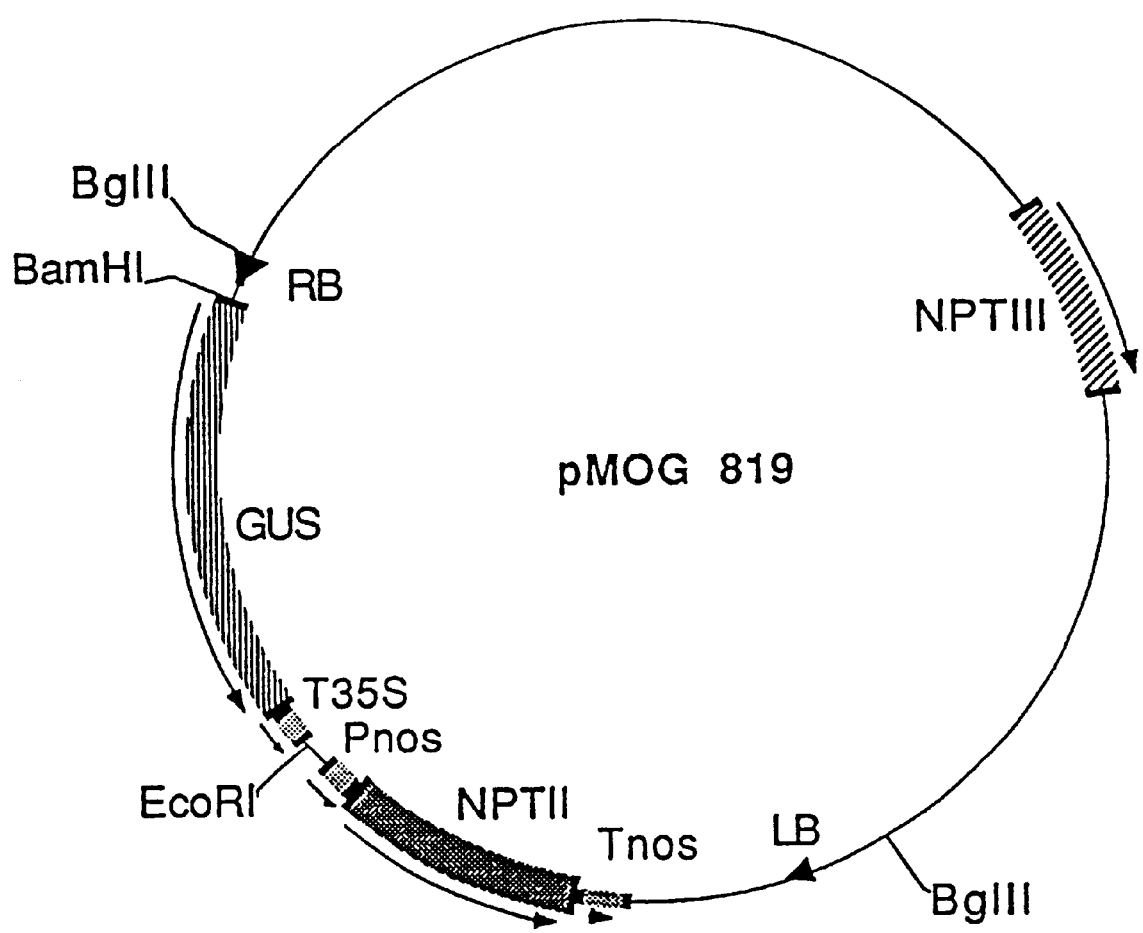
FIG. 4. Schematic plasmid map of Binary vector pMOG819.

220; 245–250) of pMOG553 as a BamHI-EcoRI fragment in the polylinker of pMOG800. The binary vector pMOG819 (FIG. 4) serves to introduce the cloned promoter fragments for further expression analysis after transformation of plants.

EXAMPLE 5

Analysis of Promoter Fragments After Re-introduction Into Arabidopsis

Figure 5:
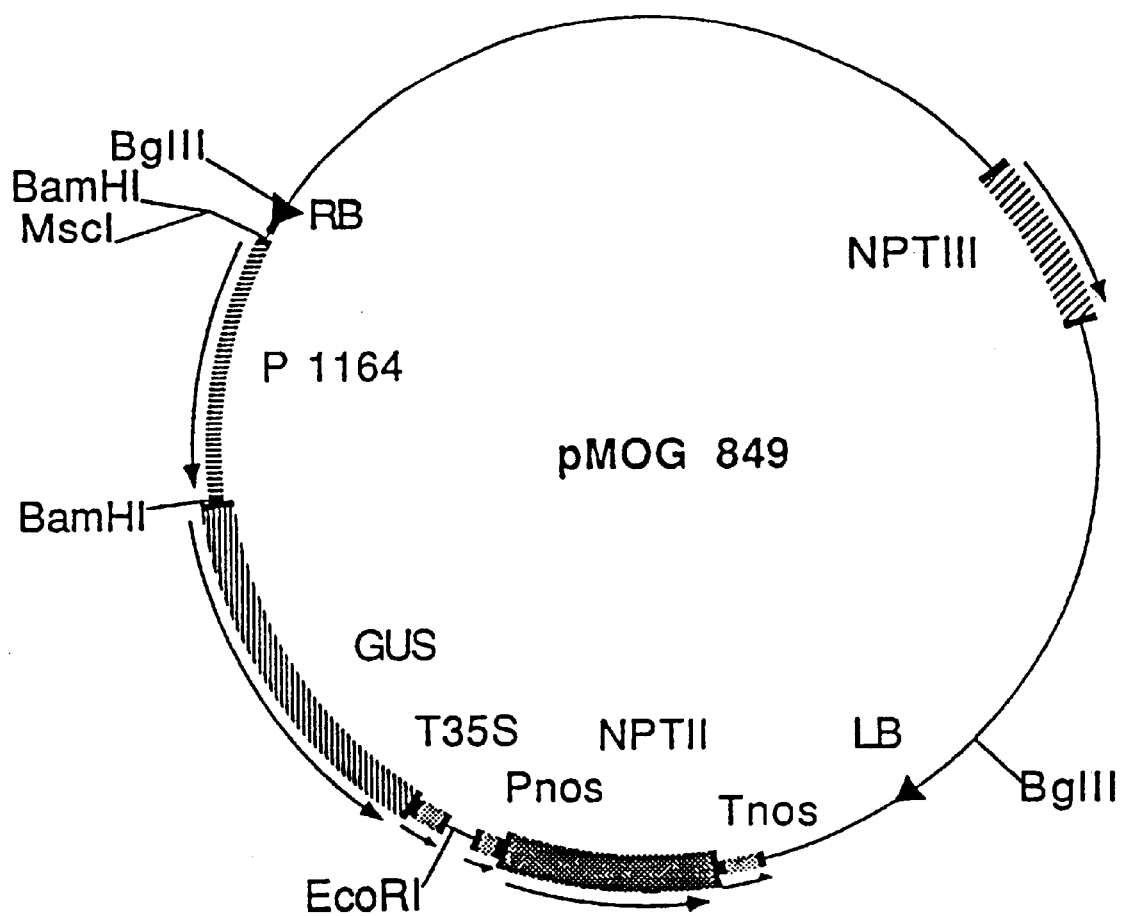
FIG. 5. Schematic plasmid map of Binary vector pMOGB49.
Figure 7:
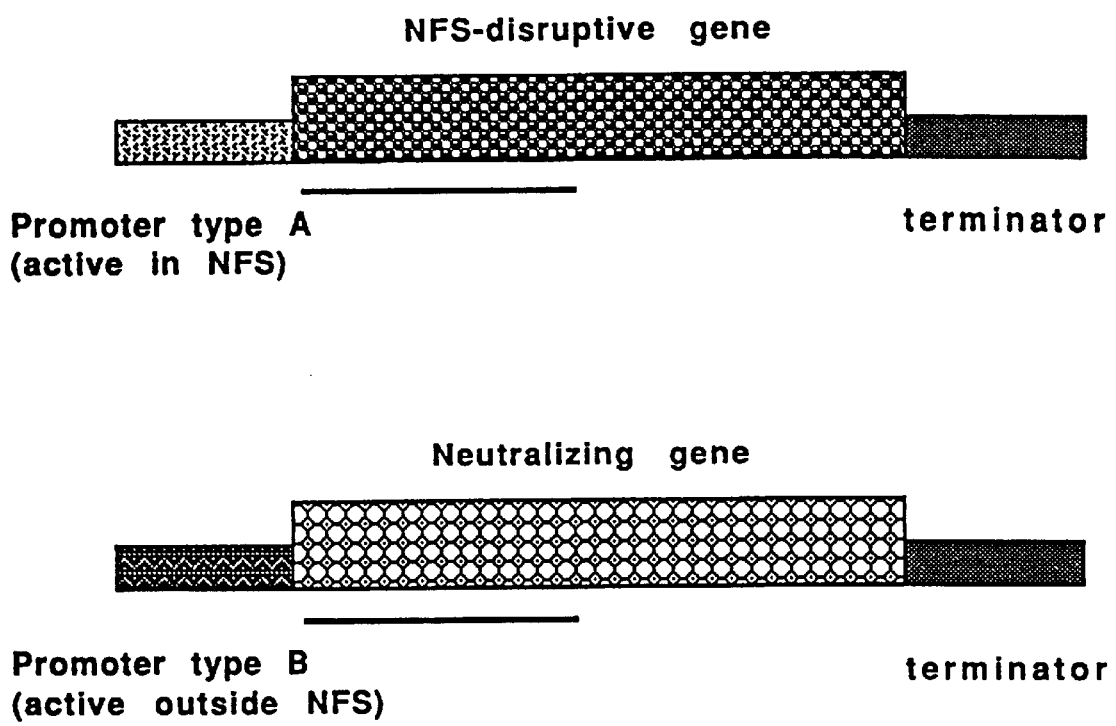
FIG. 7. Schematic representation of a NFS disrupter gene and a neutralizer gene in a two component system for engineering of nematode resistanct plants.
Figure 8:
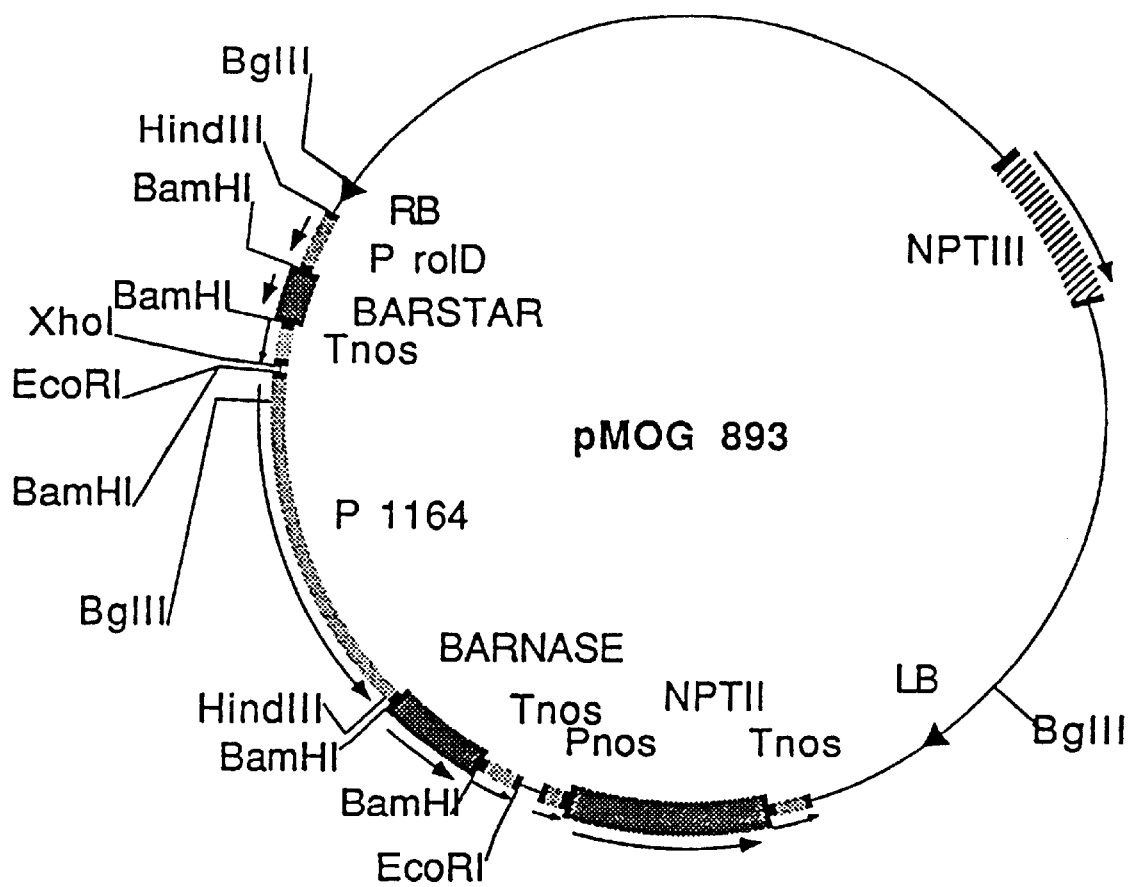
FIG. 8. Schematic plasmid map of Binary vector pMOG893.

The PCR product from tag 553#1164 was cloned back in front of a GUS gene on the binary vector pMOG819 to make pMOG849 (FIG. 5). A sample of *E. coli* DH5α harboring pMOG849 has been deposited at the Centraal Bureau voor schimmelcultures, Oosterstraat 1, Baarn, The Netherlands, on May 4, 1995 under number CBS 308.95. To determine the tissue-specific activity of the cloned promoter fragment the resulting clone pMOG849 was mobilized to *Agrobacterium tumefaciens* and the corresponding strain was used to transform wildtype *Arabidopsis thaliana* plants. Per construct 24–30 transformants were produced. Seeds from the primary transformants were harvested and grown up for infection assays with *Neterodera schachtii* as described in the Experimental part. GUS analysis after nematode infection showed that 79% of the lines transformed with pMOG849 expressed the reporter gene in syncytia. Some weak expression was also found in the area of lateral root branching, in the vascular tissue of roots and leaves, in the centre of the rozette and in some flower tissues. GUS expression outside the syncytium showed strong variation from line to line (see FIG. 6). Presumably, this variation is a result of genome position effects on the introduced regulatory sequences. Nevertheless, in most lines, an expression pattern was found that was very similar to the originally tagged line 553#1164.

Even though the activity of the promoter fragment in the various pMOG849 lines was generally much weaker than the GUS-activity inside syncytia, none of the syncytium-positive lines was entirely specific for the feeding sites.

GUS-expression was also found in giant cells induced by infection with *Meloidogyne incognita* in the same lines which expressed GUS in syncytia induced by *Heterodera schachtii*. This shows that the #1164 fragment can be used as a nearly feeding site specific promoter to engineer plants having reduced susceptibility to *Meloidogyne incognita* and *Heterodera schachtii*.

During the tissue culture phase, it was observed that the #1164 regulatory sequence was also active as a promoter, thus promoting the need to use a neutralizing gene if the #1164 promoter fragment is transferred to Arabidopsis with a plant cell disruptive gene under its control, such as barnase (see Example 8 and 9).

The 553#1164-based PCR fragment was used as a probe to isolate the corresponding genomic clone. A genomic fragment of 2.1 Kb (see SEQ ID NO: 4) was then used in a similar approach as described above (pMOG889 contains genomic 553#1164 fused to GUSintron). Again, nematode-induced GUS expression could be observed in syncytia and giant cells after nematode infection of Arabidopsis roots with *H. Schachtii* and *M. incognita* respectively.

EXAMPLE 6

Sequence determination of promoter tag pMOG553#1164

The sequence of the genomic clone of #1164 was determined by the primer walking strategy on CsCl purified DNA, using the automatic sequencer ALF of Pharmacia. Fluor DATP was used in combination with the AutoRead sequencing kit. The procedure is described in Voss et al. (1992) Mol Cell Biol 3, 153–155. The sequence is depicted in SEQ ID NO: 4.

EXAMPLE 7

Cloning of Promoter Subfragment(s)

Five subfragments of promoter #1164 were made by PCR using the primers as shown in table 4. The primer numbering is the same as that used in the Sequence Listing. For all amplifications the proofreading DNA polymerase pfu was used and pMOG849 served as target DNA. All 5' end primers contain an XhoI site. Thus, all PCR generated deletion fragments of the 1164 promoter could be reintroduced in pMOG819 using this XhoI site and the BamHI site, which is located in the multiple cloning site of pMOG553 and was retained in the tagged line1164 between the GUS coding region and the tagged plant sequence. The numbers refer to the constructs resulting from the subfragments cloned in pMOG819; the primers 6044-1 to 6044-6 correspond with SEQ ID NO's 6 to 11, respectively.

TABLE 4

| pMOG | 5' end primer | 3' end primer |
| --- | --- | --- |
| 958 | 6044-1 | 6044-6 |
| 959 | 6044-2 | 6044-6 |
| 960 | 6044-3 | 6044-6 |
| 961 | 6044-4 | 6044-6 |
| 962 | 6044-1 | 6044-5 |

After reintroduction of these gene cassettes into plants expression patterns, timing and the like can be determined as described for the 1.5 Kb #1164 fragment in Example 3. Fragments found to have useful patterns and/or timing may subsequently be used to drive expression of other heterologous DNA sequences (both sense/coding and antisense) and/or used to make hybrid promoter constructs. Furthermore, further analysis yields insight in several regulatory elements such as silencers, enhancers and the like, and creates the possibility of willfully influencing expression patterns and/or timing. To illustrate how the promoter fragments according to invention can be used to impart reduced susceptibility to nematodes this is now illustrated for the genomic 2.1 Kb #1164 fragment, cloned in front of Barnase, as an example of a NFS-disrupter gene.

EXAMPLE 8

Cloning of #1164 in Front of Barnase

A 2.1 Kb genomic DNA fragment containing the 5' tagged sequence from line 1164 was cloned in front of barnase, a *Bacillus amyloliquefaciens* derived RNase gene, to engineer plants resistant to sedentary plant nematodes. The genomic fragment was obtained by screening 400000 clones of a genomic library of *Arabidopsis ecotype* C24 with the #1164 iPCR product (see Example 3). From one of the hybridizing clones a 4 kb EcoRI fragment was isolated and subcloned in the multicopy plasmid pKS (Stratagene). Sequence analysis revealed that this clone contained 2.1 kb of sequence 5' to the T-DNA insertion in line 1164 and 1.9 kb of 3' sequence.

To restore the exact sequence context in front of the GUS coding region a 546 bp SnaBI fragment from pMOG849 spanning the promoter-GUS fusion was inserted at the SnaBI site of the genomic clone. A 2325 bp HindIII fragment was isolated from the resulting clone, containing the entire 5' tagged sequence from the genomic EcoRI subclone. This fragment was cloned in front of the barnase gene in construct pFL8 (described below), resulting in clone pFL15.

A fragment containing the barnase coding region was PCR amplified on pMT416 DNA (Hartley, sub) using primers 5' CGGACTCTGGATCCGGAAAGTG 3' (SEQ ID NO: 12) and 5' CTGCTCGAGCCTAGGCACAGGTTATCAA-CACGTTTG 3' (SEQ ID NO: 13). These primers introduce flanking BamHI and XhoI restriction sites to facilitate cloning of the fragment. The fragment was cloned in the multiple cloning site in a vector containing the barstar gene under control of a Taq promoter (necessary to overcome toxicity of barnase in bacteria). To eliminate toxicity of barnase expression in subsequent cloning steps a ST-LS1 intron was inserted in the StyI site of barnase. An NcoI site was created at the barnase translation initiation codon by recombinant PCR using the primers 5' CGGACTCTG-GATCCGGAAAGTG 3' (SEQ ID NO: 14) and 5' CTTACTCGAGCCATGGTAAGTTTCTGC 3' (SEQ ID NO: 15), resulting in pOG16.1. The 5' untranslated sequence of barnase was further modified to resemble the corresponding sequence in the original line pMOG553 #1164 by annealing the following oligonucleotides 5' GATCTA-GACTCGAGAAGCTTGGATCCCCGGGTAG-GTCAGTCCCC 3' (SEQ ID NO: 16) and 5' CATGGGG-GACTGACCTACCCGGGGATCCAAGCTTCTCGAGTCTA 3' (SEQ ID NO: 17) and ligating the resulting adapter between the BglII site and the NcoI site of pOG16.1, resulting in clone pFL8. The adapter introduced a HindIII site 5' to the barnase coding region which was used to insert the 1164 promoter yielding pFL15. In addition, by this procedure a fragment containing the Taq promoter and the barstar gene were exchanged with this adapter.

EXAMPLE 9

Construction rolD-B*

Construct pFL11 contains a chimeric barstar gene in a binary vector. This construct was cloned in the following way. The barstar coding region resides on a HindIII/BamHI fragment in construct pMT316 (Hartley (1988) J Mol Biol 202, 913–915). The HindIII site was changed into a BamHI site by ligating in this site the self-annealing adapter 5' AGCTCGGATCCG 3' (SEQ ID NO: 18). Subsequently, the resulting BamHI fragment was cloned between a double enhanced CaMV 35S promoter and a nos terminator in the expression cassette pMOG180, described in WO93/10251, resulting in pOG30. Using the adapter 5' GGCTGCTC-GAGC 3' (SEQ ID NO: 19) the HindIII site at the 3' end of the nos terminator was changed into an XhoI site and the EcoRI site at the 5' end of the promoter was changed into a HindIII site using the adapter 5' AATTGACGAAGCT-TCGTC 3' (SEQ ID NO: 20). Then the 35S promoter was replaced by the promoter from the *Agrobacterium rhizogenes* RolD gene. This promoter was excised as a HindIII/BamHI fragment from construct pDO2, obtained from F. Leach (Leach and Aoyagi (1991) Plant Sci 79, 69–76). From the resulting clone, pOG38, the barstar gene including promoter and terminator was excised by digestion with HindIII and XhoI and inserted in the respective sites of the polylinker in pMOG800, resulting in pFL11.

Finally, the chimeric #1164 promoter-barnase gene was cleaved out of pFL15 as an EcoRI fragment and inserted in the unique EcoRI site of pFL11 between barstar and the NptII marker gene in a tandem orientation, resulting in pMOG893.

EXAMPLE 10

Transformation of Potato Plants with pMOG893 and Testing for Increased Resistance Against *Globodera palida*

The binary vector pMOG893 was mobilized to *Agrobacterium tumefaciens* and the resulting strain was used for transformation of tuber discs from the potato cultivar Kardal as described in the Experimental part. A total of 98 transgenic lines were obtained. These lines were propagated vegetatively by cutting shoots in segments containing at least one node and rooting them in vitro. Per line 15 plants are tested for increased resistance to *Globodera pallida* as described in the Experimental part. It is expected that potato plants transformed with the pMOG893 contained Barnase/Barstar construct show reduced susceptibility to *Globodera pallida* due to the nematode-induced expression of Barnase inside the (developing) nematode feeding structure.

The above examples merely serve to illustrate the invention and are not meant to indicate its limits. Numerous modifications will readily occur to the person skilled in the art which are within the scope of the invention.

What is claimed is:

1. An isolated DNA fragment comprising
   (a) SEQ ID NO:4; or
   (b) a portion of SEQ ID NO:4 that is capable of promoting root knot or cyst nematode-inducible transcription of a coding sequence downstream of and operably linked to said portion in at least an *Arabidopsis thaliana* plant, wherein the fragment comprises a nucleotide sequence from SEO ID NO:4 of at least about 0.25 kilobases.

2. An isolated DNA fragment according to claim 1, wherein the fragment comprises a nucleotide sequence from SEQ ID NO:4 of at least about 1.5 kilobases.

3. An isolated DNA fragment according to claim 1, wherein the fragment comprises a nucleotide sequence from SEQ ID NO:4 of at least about 2.1 kilobases.

4. An isolated DNA fragment according to claim 1, comprising the portion of SEQ ID NO:4 of subparagraph (b).

5. An isolated DNA fragment claim according to claim 4, wherein the fragment comprises a nucleotide sequence selected from the group consisting of
   (a) nucleotides 1 to 2141 of SEQ ID NO:4;
   (b) nucleotides 646 to 2141 of SEQ ID NO:4;
   (c) nucleotides 787 to 2163 of SEQ ID NO:4;
   (d) nucleotides 1147 to 2163 of SEQ ID NO:4;
   (e) nucleotides 1853 to 2163 of SEQ ID NO:4;
   (f) nucleotides 1918 to 1940 of SEQ ID NO:4; and
   (g) nucleotides 787 to 1908 and 2128–2142 of SEQ ID NO:4.

6. A method for forming a hybrid regulatory DNA sequence comprising:
   (a) providing the isolated DNA fragment of claim 4 comprising the portion of SEQ ID NO:4; and
   (b) linking said portion to another DNA sequence to form the hybrid regulatory sequence.

7. An isolated DNA fragment according to claim 1, wherein the portion is capable of promoting said transcription preferentially in a cell of a nematode feeding structure.

8. A chimeric DNA sequence comprising in the direction of transcription the DNA fragment of claim 1, and a coding sequence not naturally under transcriptional control of said DNA fragment, said coding sequence being operably linked to and under transcriptional control of said DNA fragment.

9. A chimeric DNA sequence according to claim 8, wherein the coding sequence, when expressed in a plant cell, causes disruption of said plant cell.

10. A chimeric DNA sequence according to claim 9, wherein the coding sequence encodes an RNA transcript that is complementary to RNA essential to viability of said plant cell.

11. A chimeric DNA sequence according to claim 8, wherein the coding sequence encodes barnase.

12. A chimeric DNA sequence according to claim 8, wherein the coding sequence encodes a substance that is toxic to an inducing nematode.

13. A replicon comprising the chimeric DNA sequence of claim 8.

14. A microorganism containing a replicon according to claim 13.

15. A plant cell having incorporated into its genome the chimeric DNA sequence of claim 8.

16. A root system of a plant comprising the plant cell of claim 15.

17. A plant grafted on the root system of claim 16.

18. A method for transforming a plant comprising the steps of:
   (a) providing the chimeric DNA sequence of claim 8; and
   (b) introducing said sequence into the plant.

19. A plant comprising the plant cell of claim 15.

20. A plant according to claim 19 which is a dicotyledonous plant.

21. A plant according to claim 19 which is a potato plant.

22. A plant part selected from the group consisting of seeds, flowers, tubers, roots, leaves, fruits, pollen and wood, each comprising the plant cell of claim 15.

23. A crop comprising the plant of claim 19.

24. A replicon comprising in the direction of transcription the isolated DNA fragment of claim 1 and at least one recognition site for a restriction endonuclease for insertion of a DNA sequence to be expressed under the control of said DNA fragment.

25. A method for identifying a DNA subfragment capable of functioning as a promoter in a plant comprising the steps of:
   (a) providing the isolated DNA fragment of claim 1;
   (b) isolating a subfragment of said isolated fragment; and
   (c) testing the isolated subfragment to determine whether it is capable of promoting transcription of a coding sequence operably linked thereto in the plant.

26. An isolated DNA fragment according to claim 1, wherein said portion comprises a combination of subfragments of SEQ ID NO:4.

27. An isolated DNA fragment according to claim 26, wherein the subfragments comprise nucleotides 787 to 1908 and 2128–2142 of SEQ ID NO:4.

* * * * *